United States Patent
Ouchi (10) Patent No.: US 7,303,561 B2
(45) Date of Patent: Dec. 4, 2007

(54) HIGH-FREQUENCY TOOL FOR ENDOSCOPE

(75) Inventor: Teruo Ouchi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/962,606

(22) Filed: Oct. 13, 2004

(65) Prior Publication Data
US 2005/0080412 A1  Apr. 14, 2005

(30) Foreign Application Priority Data
Oct. 14, 2003 (JP) ............................ 2003-353584

(51) Int. Cl.
*A61B 18/14* (2006.01)
(52) U.S. Cl. ............... 606/45; 606/46; 606/48
(58) Field of Classification Search ........... 606/45, 606/46, 49
See application file for complete search history.

(56) References Cited

U.S. PATENT DOCUMENTS

| | | | |
|---|---|---|---|
| 4,362,160 A * | 12/1982 | Hiltebrandt | 606/46 |
| 6,086,583 A * | 7/2000 | Ouchi | 606/41 |
| 6,095,970 A | 8/2000 | Hidaka et al. | |
| 6,193,717 B1 | 2/2001 | Ouchi | |
| 6,689,051 B2 | 2/2004 | Nakada et al. | |
| 6,689,130 B2 * | 2/2004 | Arai et al. | 606/46 |

FOREIGN PATENT DOCUMENTS

| | | |
|---|---|---|
| JP | 9-66019 | 3/1997 |
| JP | 9-187415 | 7/1997 |
| JP | 2000-079086 | 3/2000 |
| JP | 2001-61855 | * 3/2001 |
| JP | 2002-045369 | 2/2002 |

OTHER PUBLICATIONS

English Language Abstract of JP 9-187415.
English Language Abstract of JP 2000-079086.
U.S. Appl. No. 10/959,062 to Ouchi, filed Oct. 7, 2004.
U.S. Appl. No. 10/922,956 to Ouchi, filed Aug. 23, 2004.

* cited by examiner

*Primary Examiner*—Lee S. Cohen
(74) *Attorney, Agent, or Firm*—Greenblum & Bernstein, P.L.C.

(57) ABSTRACT

A high-frequency treatment tool for an endoscope is provided with a transparent hood to be detachably coupled to a distal end of an endoscope provided with at least one electrode, at least one high-frequency electrode provided at a tip end of the transparent hood, at least one contact which is to electrically contact the at least one electrode of the endoscope, and at least one conductive member that electrically connects the at least one high-frequency electrode and the at lease one contact. The at least one conductive member is arranged to be located at an inner position with respect to an outer surface of the transparent hood.

8 Claims, 10 Drawing Sheets

HIGH-FREQUENCY TOOL FOR ENDOSCOPE

BACKGROUND OF THE INVENTION

The present invention relates to a high-frequency tool for an endoscope.

The high-frequency tool for the endoscope is typically attached to a tip of an inserting section of the endoscope for a treatment such as incision or coagulation of the mucous of human tissues.

Since a high-frequency electrical current flows through the high-frequency tool, it is generally configured such that a high-frequency electrode is attached at the tip of a flexible electrically-insulating tube, which is inserted through a treatment tool channel of the endoscope.

In some cases, however, treatment cannot be done well with the high-frequency tool configured as above. As an alternative, a high-frequency tool configured such that a high-frequency electrode is provided to a hood that is detachably attached onto the tip of the inserting section of the endoscope has been suggested. An example of such a tool is disclosed in Japanese Patent Provisional Publication No. HEI 09-0187415.

In the above publication, besides channel(s) formed in the endoscope body, another channel is provided outside the endoscope and the hood, and the high-frequency snare is inserted therethrough. According to this structure, depending on the high-frequency tool, lead lines for supplying electrical current to the electrodes of the high-frequency tool mounted on the hood may be run outside the inserting section of the endoscope.

According to the publication above, since the high-frequency electrode is provided to the detachable hood coupled to the tip of the endoscope, a lead line supplying the electrical current to the electrode is hung around the inserting section and swings around the inserting section of the endoscope, Thus, the lead lines are troublesome for an operator since they may twine his/her hand and obstruct the operation of the endoscope. However, if the lead lines are inserted into the channel for a treatment tool, other tools such as a suction tool and the like cannot be used simultaneously.

SUMMARY OF THE INVENTION

The present invention is advantageous in that an improved high-frequency tool for an endoscope is provided. The endoscope has a detachably coupled tip hood that functions as a base for the high-frequency tools, and can be used without imposing burden to both the patient and the operator.

According to the invention, there is provided a high-frequency treatment tool for an endoscope, which is provided with a transparent hood to be detachably coupled to a distal end of an endoscope provided with at least one electrode, at least one high-frequency electrode provided at a tip end of the transparent hood, at least one contact which is to electrically contact the at least one electrode of the endoscope, and at least one conductive member that electrically connects the at least one high-frequency electrode and the at least one contact, the at least one conductive member being arranged to be located at an inner position with respect to an outer surface of the transparent hood.

Optionally, the at least one high-frequency electrode may include a linear electrode connecting two positions spaced from each other when viewed from a front of the tip end of the transparent hood.

In this case, the two positions may be opposite positions with respect a center of the high-frequency tool when viewed from the front of the tip end of the transparent hood.

Further, the linear electrode may be formed of an electrically conductive wire.

Still optionally, the at least one contact includes a single contact, while the at least one conductive member may include two conductive members. Ends of the two conductive members may be connected with the linear electrode at the two positions, respectively. The other ends of the two conductive members may be connected with the single contact.

Further optionally, the at least one contact may include two contacts, the at least one conductive member includes two conductive members, ends of the two conductive members being connected with the linear electrode at the two positions, respectively, the other ends of the two conductive members being connected with the two contacts, respectively, only one of the two contacts being supplied with a high-frequency electrical current.

Still optionally, the at least one high-frequency electrode may include two electrodes, at least one contact may include two contacts, and the at least one conductive member may include two conductive members, the two contacts connecting the two electrodes with the two contacts, respectively, In a particular case, the two electrodes may be arrange to be spaced from each other when viewed from the tip end side of the transparent hood.

Alternatively, the two electrodes may be located at opposite positions with respect a center of the high-frequency tool when viewed from the tip end side of the transparent hood.

Still optionally, at least a part of the at least one conductive member may be arranged to extend along an inner wall of the transparent hood.

Alternatively or optionally, at least a part of the at least one conductive member may be buried in a body of the transparent hood.

DETAILED DESCRIPTION OF THE EMBODIMENTS

Referring now to the accompanying drawings, high-frequency tools according to three embodiments of the present invention will be described.

First Embodiment

Figure 1:
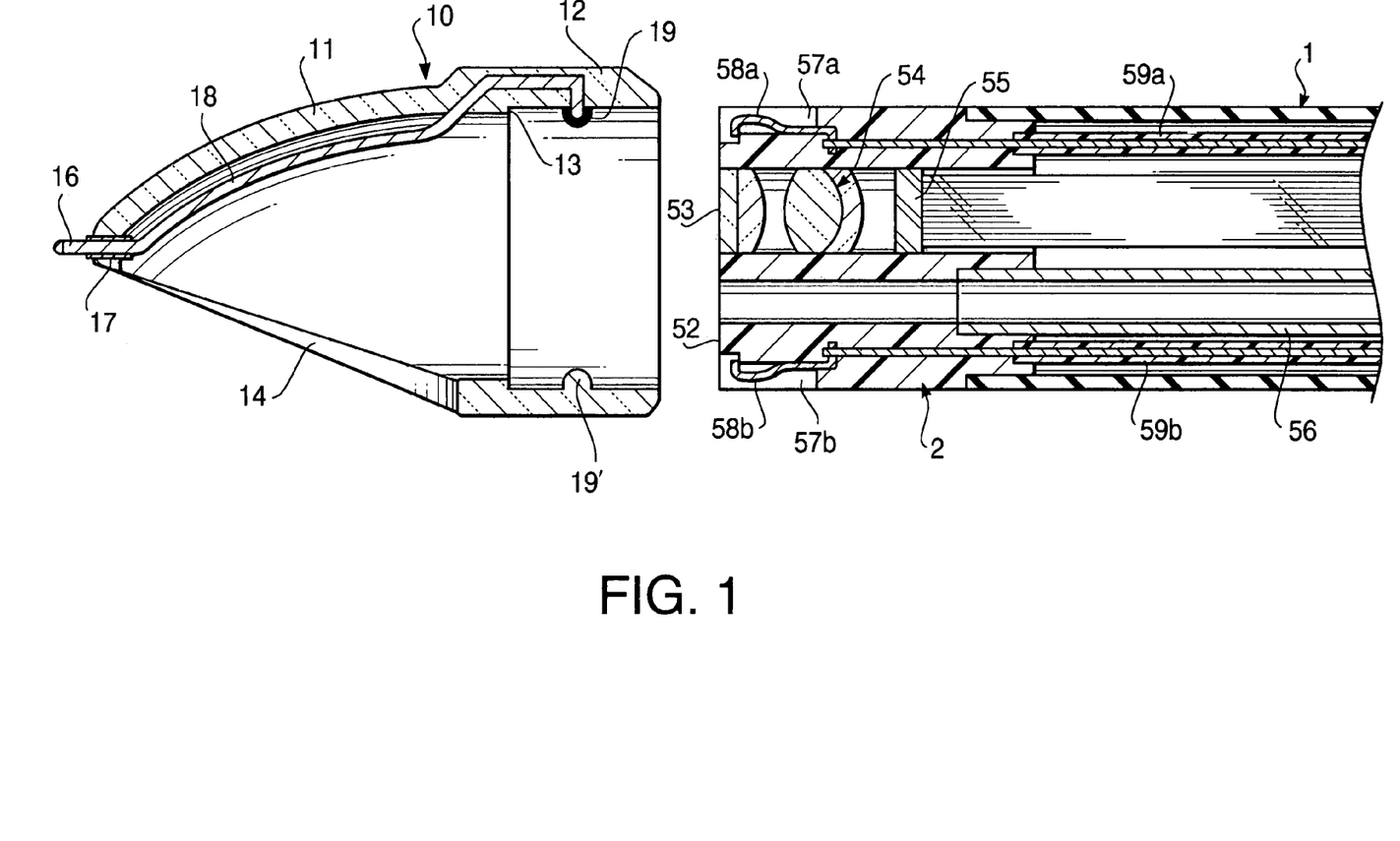
FIG. 1 shows a cross-sectional view of a high-frequency tool according to a first embodiment of the invention and a tip portion of the inserting section of an endoscope to which the high-frequency tool is coupled.
Figure 2A:
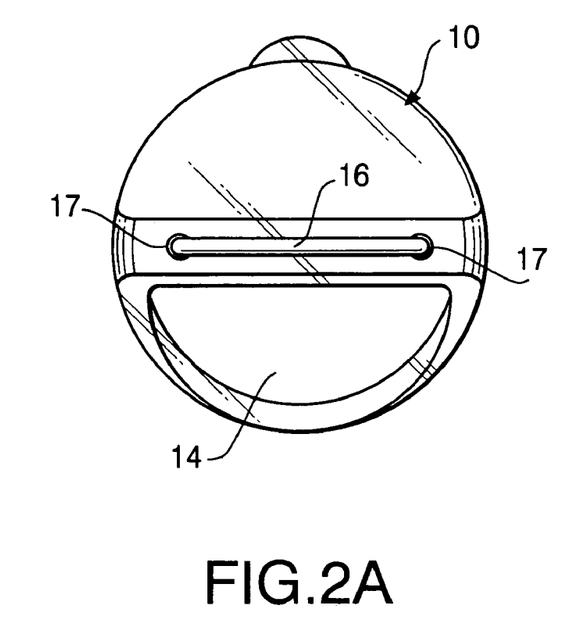
FIG. 2A is a front view of the high-frequency tool according to the first embodiment.
Figure 2B:
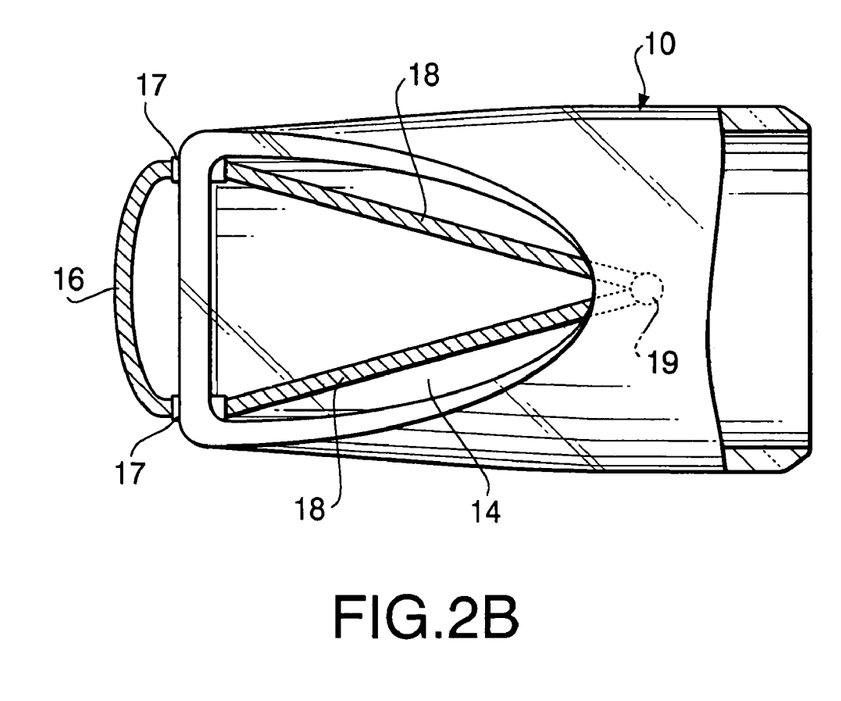
FIG. 2B is a partially cross-sectional bottom view of the high-frequency tool according to the first embodiment.
Figure 3:
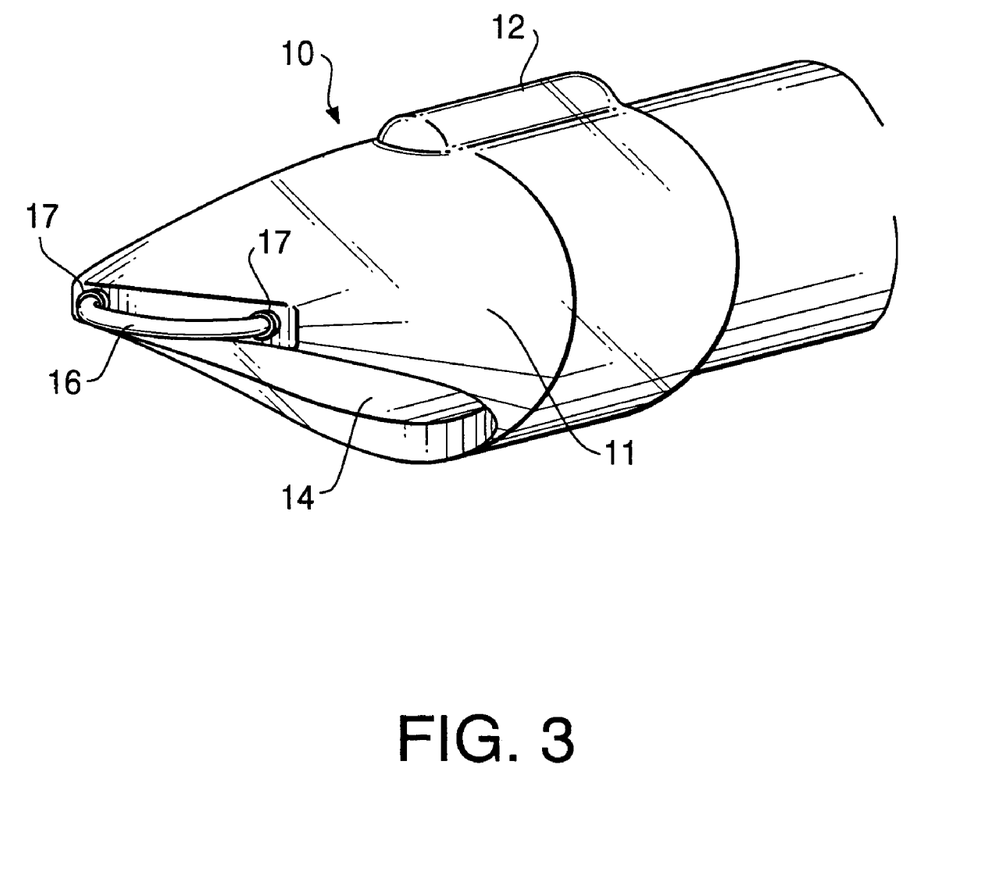
FIG. 3 is a perspective view of the high-frequency tool according to the first embodiment.

FIG. 1 shows a cross-sectional view of a high-frequency tool according to a first embodiment of the invention and a tip portion of the inserting section 1 of an endoscope to which the high-frequency tool 10 is coupled, FIG. 2A is a front view of the high-frequency tool 10, FIG. 2B is a partially cross-sectional bottom view of the high-frequency tool 10, and FIG. 3 is a perspective view of the high-frequency tool 10.

In the example shown in FIG. 1, the endoscope is a so-called front view type endoscope, which is configured such that an observing window 53 for observing an object in front of a tip end surface 52 of the endoscope is provided on the tip end surface 52. It should be noted that, according to the invention, the endoscope may be an oblique-front view type.

As shown in FIG. 1, the tip end portion has a tip end body 2, which has the tip end surface 52. Light from the object is incident on the observing window 53 and converged by an objective optical system 54. The converged light forms an image of the object on a image capturing surface of a solid state imaging element 55 (e.g., a CCD: Charge Coupled Device). Alternatively, instead of the imaging element, an image guide fiber bundle is provided through the endoscope, and the image formed by the objective optical system may be formed on an end side surface of the light guide fiber bundle. In FIG. 1, 56 denotes a treatment tool insertion channel through which various tools can be inserted for treatment. An outlet of the treatment tool insertion channel is located on the tip end side surface 52.

A main body of the high-frequency tool 10 is a transparent hood 11 formed of acrylic resin or polycarbonate resin. An endoscope side of the hood 11 is formed to have a cylindrical shape having an inner diameter substantially equal to an outer diameter of the tip end body 2 so that the hood 11 surrounds the tip end surface 52. The hood 11 is detachable coupled to the tip end body 2.

On the inner wall of the hood 11, a stepped portion 13 is formed. As the hood 11 is fitted on the tip end body 2, the end surface 52 abuts the stepped portion 13 (i.e., an end surface of a smaller diameter portion), thereby the axial position of the hood 11 with respect to the tip end body 2 is adjusted.

A tip end half of the hood 11 is formed to have a shape which is the cylindrical shape collapsed and slightly curved in its axial direction. Further, an opening 14 is formed on a portion opposite to the collapsed-shape portion.

Since the opening 14 is formed, which is located in front of the treatment tool insertion channel 56, it is possible to locate a treatment tool inserted through the channel 56 to protrude out of the hood 11 through the opening 14.

As shown in FIG. 1, at the tip of the hood 11, a monopolar high-frequency electrode 16 is protruded toward the front side, which is to be contacted with the mucous and the like. Since the hood 11 is formed of the transparent resin, the high-frequency electrode 16 and its surroundings can be observed from the observing window 53 through the hood 11.

It is convenient if the depth of field of the observing optical system 54 is appropriate for such an observation. In an example, a distance from the observation window 53 and the high-frequency electrode 16 is slightly longer than 10 mm, operability of the high-frequency tool 10 is improved.

The high-frequency electrode 16 is formed from a conductive wire. As shown in FIGS. 1-3, a pair of ceramic heat-resisting pipes 17 spaced from each other are penetrated through the tip end of the hood 11 in the axial direction of the tip end body 2. The wire forming the high-frequency electrode 16 is inserted through the pair of ceramic heat-resisting pipes 17 so that the wire (i.e., the electrode 16) is stretched therebetween, outside the hood 11.

On the inner surface of the hood 11, at a position on the endoscope side with respect to the stepped portion 13, a contact 19 is protruded. The contact 19 contacts a contact 58a provided on the outer surface of the tip end body 2 when the hood 11 is attached to the tip end body 2.

The electrode 16 and the contact 19 are connected with conductive members 18, which are arranged to extend along the inner surface of the hood 11. As shown in FIG. 1, a part of each conductive member 18 is buried inside the hood 11, at the coupling part 12. On the inner wall of the hood 11, at a position opposite to the contact 19 (i.e., 180° spaced from the contact 58a), a dummy contact 19' is provided. As shown in FIG. 1, the tip end body 2 is provided with another electrode 58b, which is not used in the first embodiment, and the dummy contact 19' contacts the electrode 58b.

On the outer surface of the tip end body 2, a pair of grooves 57a and 57b reaching the end surface 52 are formed at positions corresponding to the contact 19 and the dummy contact 19'. The electrode 58a that contacts the contact 19 when the hood 11 is fitted on the tip end body 2 is arranged inside the groove 57a, and the other electrode 58b to contact the dummy contact 19' is arranged inside the groove 57b.

Each electrode 58a (58b) is formed from conductive and elastic metal plate. A distal end side half (i.e., a left-hand side half in FIG. 1) of each electrode 58a (58b) is formed to have a portion which is curved to expand outward so that it interferes with the contact 19 (19') when the hood 11 is fitted on the tip end body 2.

Figure 4:
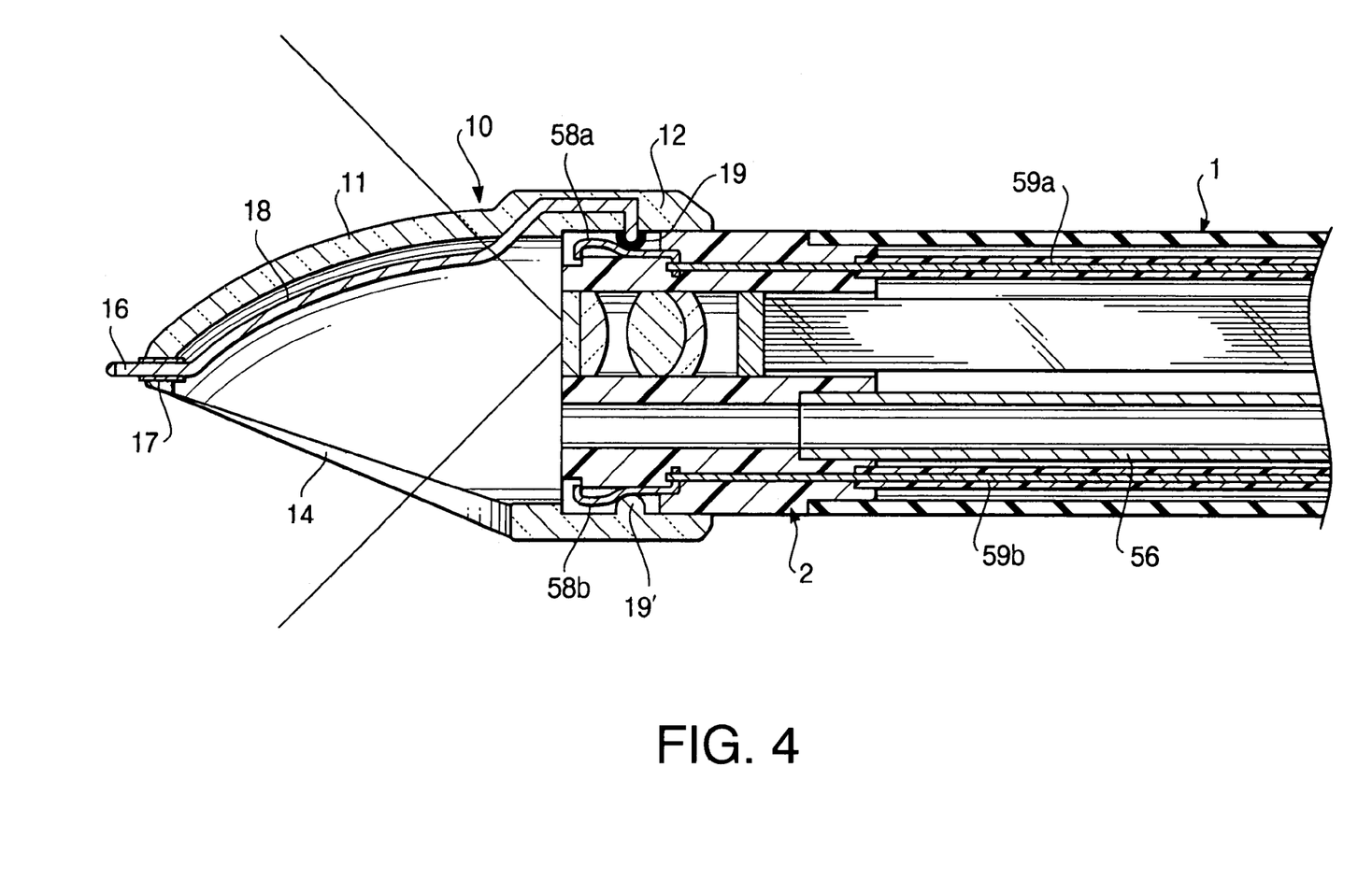
FIG. 4 is a cross-sectional view of the high-frequency tool according to the first embodiment coupled to the tip portion of the inserting section of the endoscope.

When the hood 11 is coupled to (i.e., fitted on) the tip end body 2, the electrodes 58a and 58b are pressed inward by the contact 19 and the dummy contact 19' and elastically deform, respectively. When the hood 11 is completely coupled (i.e., when the end surface 52 contacts the stepped portion 13), the electrodes 58a and 58b return to their original shapes by the elasticity thereof with keep contacting the contact 19 and dummy contact 19', respectively, as shown in FIG. 4.

As a result, the electrodes 58a and 58b function as click springs for elastically retaining the transparent hood 11 in position. That is, the hood 11 fitted on the tip end body 2 is kept in position by the elastic force of the electrodes 58a and 58b.

In order to detach the hood 11 from the tip end body 2, the hood 11 is pulled strongly. The, the contact 19 and the dummy contact 19' slide along the grooves 57a and 57b with elastically deforming the electrodes 58a and 58b, respectively, thereby the hood 11 being detached from the tip end body 2. After the hood 11 is detached from the tip end body 2, the electrodes 58a and 58b return to their original shapes.

To the electrodes 58a and 58b, a pair of lead lines 59a and 59b are connected, respectively. When the transparent hood 11 is attached to the tip end body 2, through the contact between the electrode 58a and the contact 19, the high-frequency electrode 16 is connected with the lead line 59a.

Figure 5:
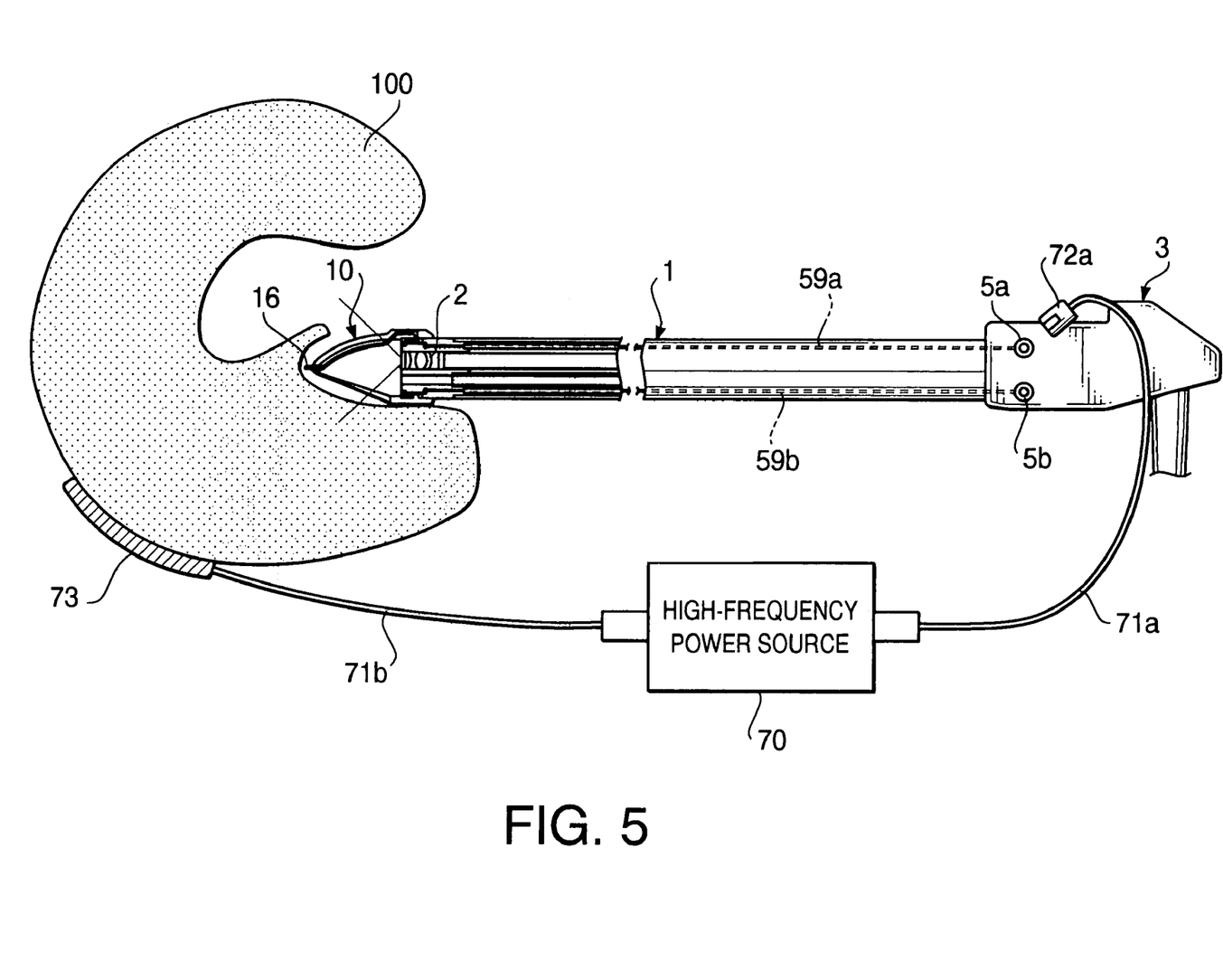
FIG. 5 schematically shows an arrangement of the endoscope coupled with the high-frequency tool according to the first embodiment when incision of mucous of human tissues is carried out.

The proximal ends of the pair of lead lines 59a and 59b are connected with power source terminals 5a and 5b, respectively, as shown in FIG. 5. The power source terminals 5a and 5b are provided on a side surface of an operation section 3 of the endoscope.

According to the first embodiment, the power source terminal 5a is connected with one output terminal of a high-frequency power source 70. Specifically, the high-frequency power source 70 has a pair of high-frequency power supply cords 71a and 71b. At the distal end of the power supply cord 71a, a plug 72a is provided, which can be detachably connected with the power source terminal 5a.

Further, according to the first embodiment, at the distal end of the power supply cords 71b, an opposite pole electrode plate 73 is connected, which is to be located outside a patient.

When the hood 11 is attached to the tip end body 2, and the plug 72a is connected to the power source terminal 5a, the high-frequency electrode 16 is connected to the high-frequency power source 70. By locating the opposite pole electrode plate 73 outside the patient and locating the high-frequency electrode 16 at a target inside the cavity of the patient, the high-frequency treatment such as the excision or exsecsion of mucous of human tissues at a position where the high-frequency electrode 16 contacts can be performed.

It should be noted that, since the lead lines 59a and 59b are buried in the body of the inserting section 1 (the lead line 59b not being necessary in the first embodiment), they do not tangle around the inserting section 1. Therefore, for both the patient and operator, the lead lines 59a and 59b do not cause difficulties and/or pain, which was unavoidable in the conventional endoscopes.

Further, since the no lead lines are inserted through the treatment tool channel 56, suction via the treatment tool channel 56 or inserting a treatment tool therethrough can be performed.

The invention is not limited to the above-described exemplary embodiment, and various modifications can be made without departing from the scope of the invention.

Second Embodiment

Figure 6A:
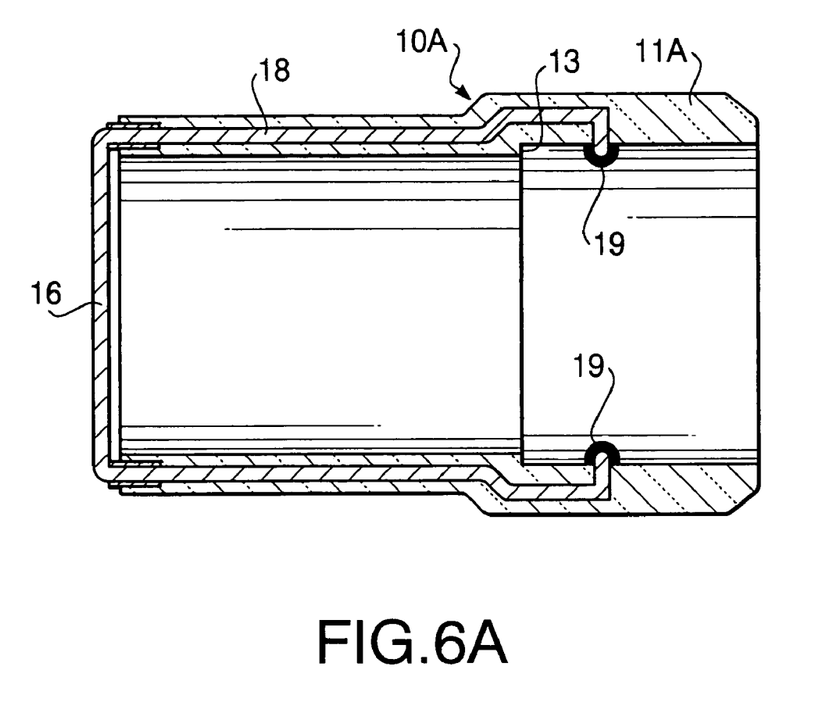
FIG. 6A is a cross-sectional side view of a high-frequency tool according to a second embodiment.
Figure 6B:
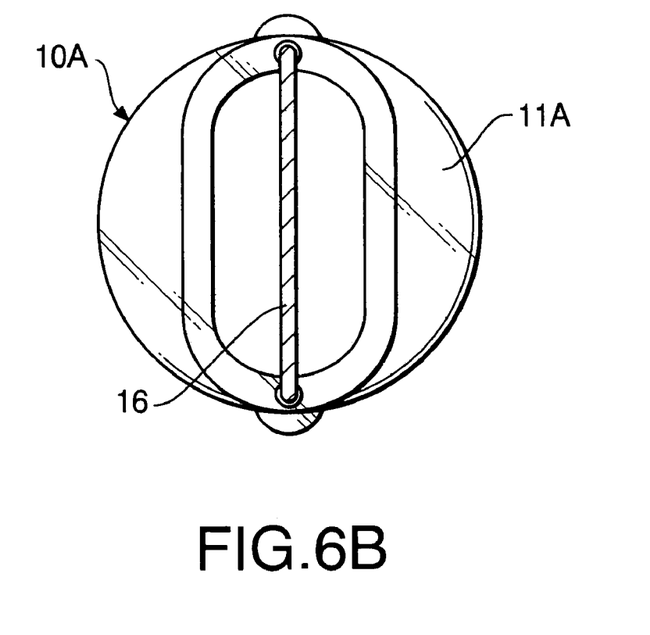
FIG. 6B is a front view of the high-frequency tool according to the second embodiment.
Figure 7:
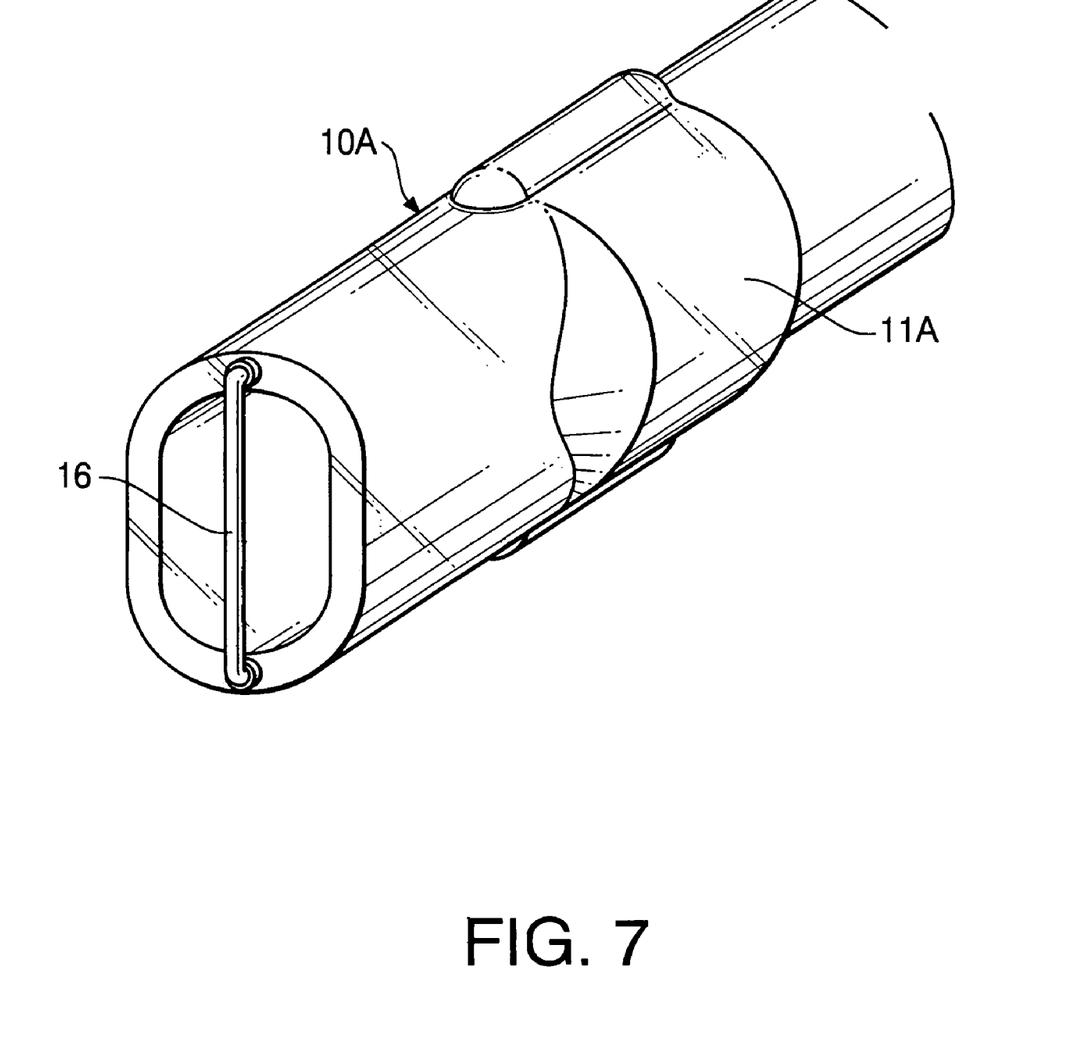
FIG. 7 is a perspective view of the high-frequency tool according to the second embodiment.

FIG. 6A is a cross-sectional side view of a high-frequency tool 1A according to a second embodiment, FIG. 6B is a front view of the high-frequency tool 10A shown in FIG. 6A, and FIG. 7 is a perspective view of the high-frequency tool 10A shown in FIGS. 6A and 6B.

As shown in FIGS. 6B and 7, a front side portion of a transparent hood 11A may be formed to be collapsed to have a shape of an elongated circle or rounded rectangle. Alternatively, the entire body of the hood may be formed to have another shape such as a cylindrical shape.

In the second embodiment shown in FIGS. 6A, 6B and 7, the conductive members 18 are entirely buried in the body of the hood 11A, and both ends of the conductive member are connected with contacts 19a and 19b, which are provided corresponding to the electrodes 58a and 58b (see FIG. 1) of the endoscope. Since the high-frequency tool 10A shown in FIGS. 6A, 6B and 7 is a monopole type tool, only one of the contacts 19a and 19b is applied with the high-frequency electrical current. Specifically, when the plug 72a is connected with the power source terminal 5a, only the contact 19a is supplied with the electrical current.

Third Embodiment

Figure 8A:
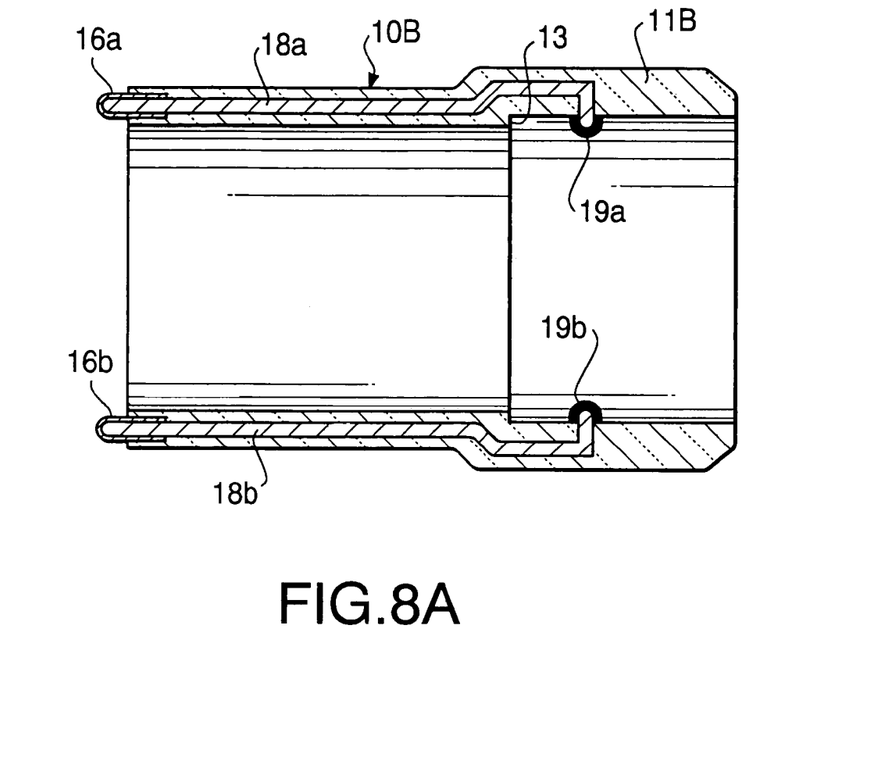
FIG. 8A is a cross-sectional side view of a high-frequency tool according to a third embodiment.
Figure 8B:
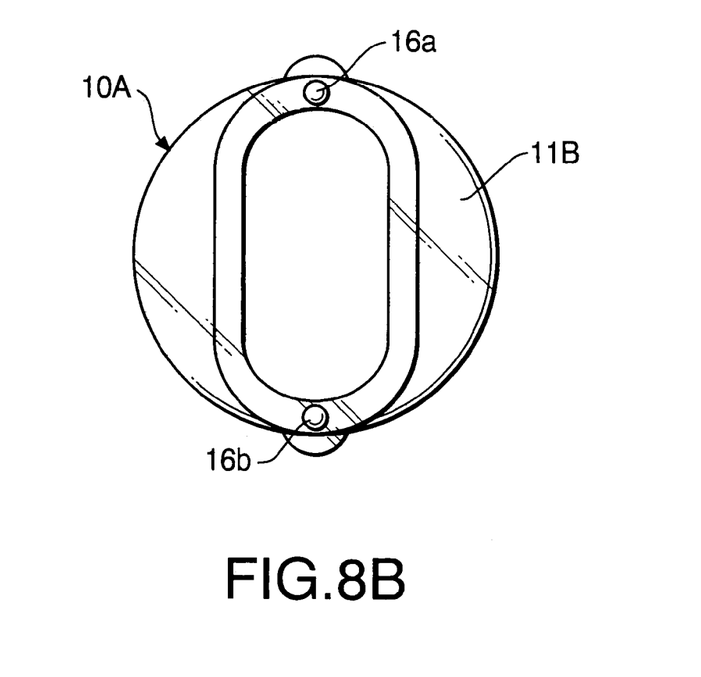
FIG. 8B is a front view of the high-frequency tool according to the third embodiment.
Figure 9:
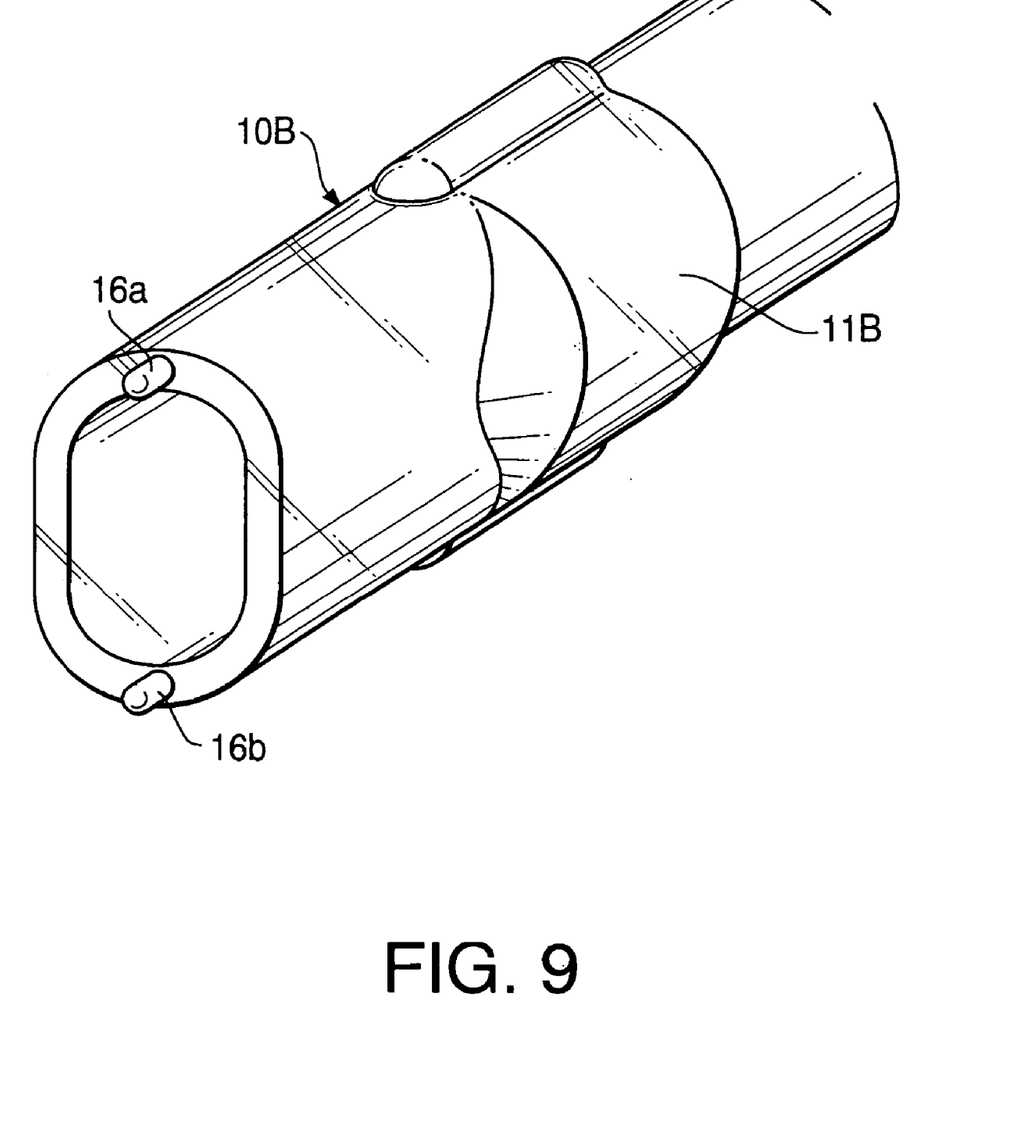
FIG. 9 is a perspective view of the high-frequency tool according to the third embodiment.
Figure 10:
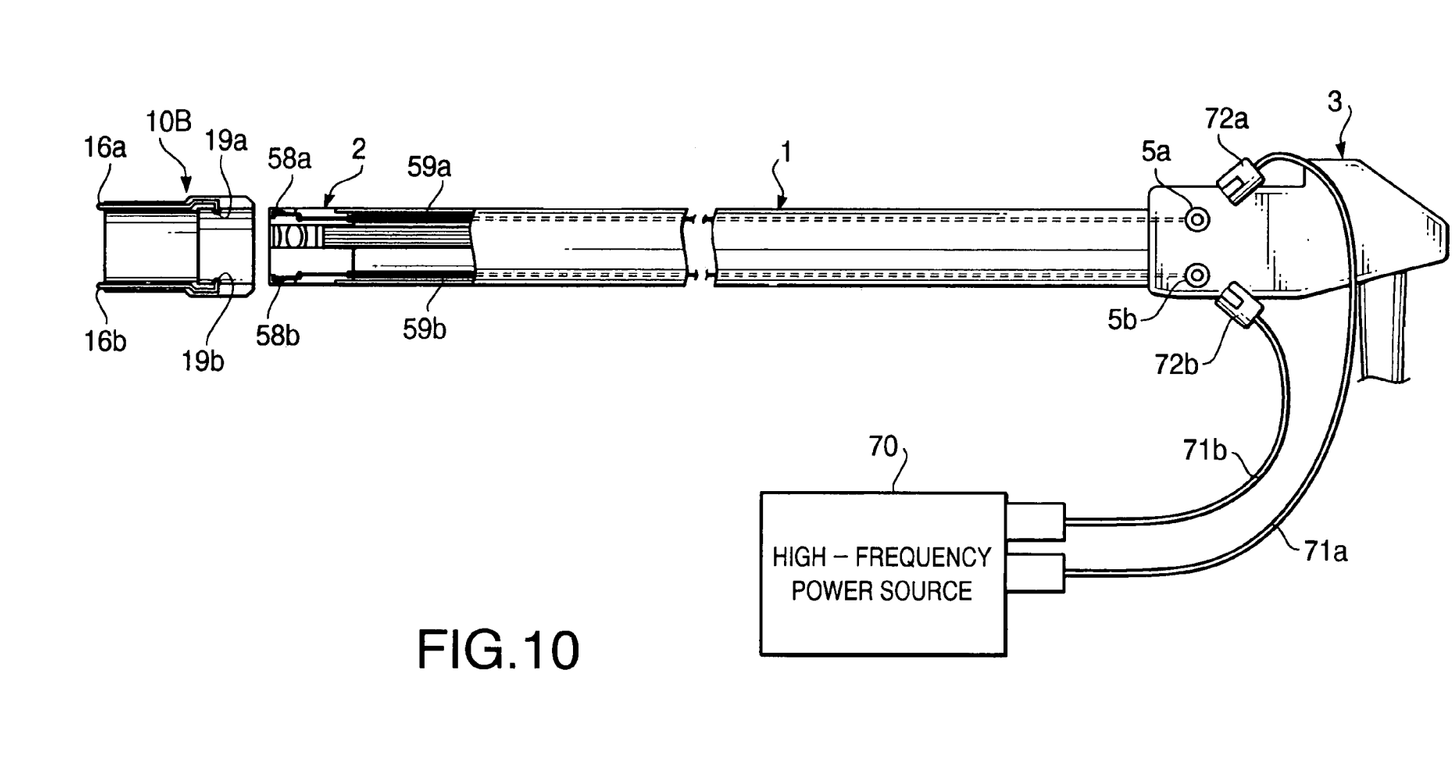
FIG. 10 schematically shows a configuration of the endoscope and the high-frequency tool according to the third embodiment.

FIG. 8A is a cross-sectional side view of a high-frequency tool 10B according to a third embodiment, FIG. 8B is a front view of the high-frequency tool 10B shown in FIG. 8A, and FIG. 9 is a perspective view of the high-frequency tool 10B shown in FIGS. 8A and 8B. FIG. 10 schematically shows a configuration of the endoscope and the high-frequency tool 10B according to the third embodiment.

The high-frequency tool 10B is a bipolar type tool. A pair of high-frequency electrodes 16a and 16b are protrude at the tip end side surface of a transparent hood 11B. A pair of conductive members 18a and 18b are provided to connect the pair of high-frequency electrodes 16a and 16b to a pair of contacts 19a and 19b, respectively. Similar to the second embodiment, the pair of contacts 19a and 19b are located at positions corresponding to the electrodes 58a and 58b, respectively.

In the third embodiment, opposite electrical voltages are applied to the pair of high-frequency electrodes 16a and 16b. Therefore, as shown in FIG. 10, at the distal end of the opposite pole cord 71b, a plug 72b is connected, which is to be connected with the power source terminal 5b.

When the hood 11B is coupled to the tip end body 2 of the endoscope and the plugs 72a and 72b are respectively connected with the power source terminals 5a and 5b, the high-frequency electrodes 16a and 16b are connected with the high-frequency power source 70.

As shown in FIGS. 8B and 9, a front side portion of a transparent hood 11B may be formed to be collapsed to have a shape of an elongated circle or rounded rectangle similarly to the second embodiment. Alternatively, the entire body of the hood may be formed to have another shape such as a cylindrical shape.

In the second and third embodiments, the pair of contacts 19a and 19b are arranged to be spaced by 180°. The invention need not be limited to such a configuration, and the positions of the contacts 19a and 19b may be varied. In such a case, the positions of the electrodes 58a and 58b may also be changed corresponding to the positions of the contacts 19a and 19b.

The present disclosure relates to the subject matter contained in Japanese Patent Application No. 2003-353584, filed on Oct. 14, 2003, which is expressly incorporated herein by reference in its entirety.

What is claimed is:

1. A high-frequency treatment tool for an endoscope, comprising:

a transparent hood to be detachably coupled to a distal end of an endoscope provided with at least one electrode;

at least one high-frequency electrode formed of an electrically-conductive wire and provided at a tip end of the transparent hood;

at least one contact which is to electrically contact the at least one electrode of the endoscope;

a pair of spaced pipes penetrating a tip end of the hood and receiving opposing ends of the high-frequency electrode; and at least one conductive member that electrically connects the at least one high-frequency electrode and the at least one contact, the at least one conductive member being arranged to be located at an inner position with respect to an outer surface of the transparent hood.

2. The high-frequency treatment tool according to claim 1, wherein the at least one high-frequency electrode includes a linear electrode connecting two positions spaced from each other when viewed from a front of the tip end of the transparent hood.

3. The high-frequency treatment tool according to claim 2, wherein the two positions are opposite positions with respect a center of the high-frequency tool when viewed from the front of the tip end of the transparent hood.

4. The high-frequency treatment tool according to claim 2, wherein the linear electrode is formed of an electrically conductive wire.

5. The high-frequency treatment tool according to claim 2, wherein the at least one contact includes one contact, the at least one conductive member includes two conductive members, ends of the two conductive members being connected with the linear electrode at the two positions, respectively, the other ends of the two conductive members being connected with the one contact.

6. The high-frequency treatment tool according to claim 2, wherein the at least one contact includes two contacts, the at least one conductive member includes two conductive members, ends of the two conductive members being connected with the linear electrode at the two positions, respectively, the other ends of the two conductive members being connected with the two contacts, respectively, only one of the two contacts being supplied with a high-frequency electrical current.

7. The high-frequency treatment tool according to claim 1, wherein at least a part of the at least one conductive member is arranged to extend along an inner wall of the transparent hood.

8. The high-frequency treatment tool according to claim 1 wherein at least a part of the at least one conductive member is buried in a body of the transparent hood.

* * * * *